(12) United States Patent
Deasy et al.

(10) Patent No.: US 6,792,073 B2
(45) Date of Patent: Sep. 14, 2004

(54) METHOD AND APPARATUS FOR RADIOTHERAPY TREATMENT PLANNING

(75) Inventors: Joseph O. Deasy, St. Louis, MO (US); Mladen Victor Wickerhauser, University City, MO (US)

(73) Assignee: Washington University, St. Louis, MO (US)

( * ) Notice: Subject to any disclaimer, the term of this patent is extended or adjusted under 35 U.S.C. 154(b) by 124 days.

(21) Appl. No.: 09/850,533

(22) Filed: May 7, 2001

(65) Prior Publication Data

US 2002/0027971 A1 Mar. 7, 2002

Related U.S. Application Data

(60) Provisional application No. 60/201,959, filed on May 5, 2000.

(51) Int. Cl.[7] ................................................. A61N 6/10
(52) U.S. Cl. ............................................ 378/65; 378/64
(58) Field of Search ..................................... 378/64, 65

(56) References Cited

U.S. PATENT DOCUMENTS

| | | | | |
|---|---|---|---|---|
| 6,301,329 | B1 | 10/2001 | Surridge ........................ | 378/65 |
| 2002/0027971 | A1 * | 3/2002 | Deasy et al. .................. | 378/65 |
| 2002/0106054 | A1 * | 8/2002 | Caflisch et al. ............... | 378/65 |

FOREIGN PATENT DOCUMENTS

WO     WO 99/40523     8/1999

OTHER PUBLICATIONS

Buffa, F. et al. "Influence of Statistical Fluctuations in Monte–Carlo Dose Calculations". Medical Physics, vol. 26, No. 6, Jun. 1999, pp. 1120–1120, XP001031982.

Jiang, Steve B. et al. "Removing the effect of statistical uncertainty on dose–volume histograms from Monte Carlo dose calculations". Phys. Med. Biol., vol. 45, 2000, pp. 2151–2161.

Mackie, T. Rockwell et al. "Tomotherapy: Optimized Planning and Delivery of Radiation Therapy". International Journal of Imaging Systems and Technology, Spring 1995, vol. 6, No. 1, pp. 43–55, XP000620333.

Petti, P.L. et al. "Investigation of buildup dose from electron contamination of clinical photon beams". Med. Phys., vol. 10, No. 1, Jan./Feb. 1983, pp. 18–24.

Sempau, J. et al. "Towards the elimination of Monte Carlo statistical fluctuation from dose volume histograms for radiotherapy treatment planning". Physics in Medicine and Biology, Jan. 2000, IOP Publishing, UK, vol. 45, No. 1, pp. 131–157, XP002185777.

Tabata, T; Andreo, P.; Ito, R. *Energy–Deposition Distributions in Materials Irradiated by Plane–Parallel Electron Beams with Energies Between 0.1 and 100 MeV*. Atomic Data and Nuclear Data Tables, vol. 56, 1994 pp. 105–131.

* cited by examiner

*Primary Examiner*—David V Bruce
(74) *Attorney, Agent, or Firm*—Woodcock Washburn LLP

(57) ABSTRACT

A computationally efficient and accurate procedure for calculating radiation dose distributions within a volume of interest in a patient incorporating variations in patient density and source particle energy, position, direction, and type. The procedure iteratively simulates energy depositions from source particles using the Monte Carlo radiation transport method and then applies methods for reducing noise inherent in Monte Carlo results to obtain an accurate and computationally efficient representation of an actual radiation dose distribution compared to that produced by Monte Carlo methods alone. The invention makes an analogy between real measured data and transformed Monte Carlo generated computer data and then applies data denoising techniques to reduce the noise in the Monte Carlo dose images. Conversely, the present invention can produce a dose distribution having a predetermined noise level in a reduced amount of computation time. Denoising techniques can include digital filtering, wavelet denoising, kernel smoothing and non-parametric regression smoothing.

33 Claims, 6 Drawing Sheets

Homogeneous phantom | Step-heterogeneity phantom

High density

Low density

Denoised using LLS_W5_O3

METHOD AND APPARATUS FOR RADIOTHERAPY TREATMENT PLANNING

RELATED APPLICATIONS

The present application claims priority from provisional application No. 60/201,959, filed May 5, 2000, entitled "Method of Radiotherapy Treatment Planning", which is incorporated in its entirety herein by reference.

FIELD OF THE INVENTION

This invention relates generally to accelerating Monte Carlo calculations, and more particularly to determining radiation dose distributions in a patient for radiotherapy treatment planning by accelerating Monte Carlo dose distribution calculations through denoising of raw Monte Carlo dose distributions.

BACKGROUND OF THE INVENTION

Medical equipment for radiation therapy treats tumorous (malignant) tissue with high energy radiation. The amount of radiation and its placement must be accurately controlled to ensure that the tumor receives sufficient radiation to be destroyed and that damage to the surrounding and adjacent non-tumorous tissue is minimized.

Internal source radiation therapy (referred to as brachytherapy) places capsules of radioactive material inside the patient in proximity to the tumorous tissue. Dose and placement are accurately controlled by the physical positioning of the isotope. However, internal source radiation therapy has disadvantages similar to those present with surgically invasive procedures, which include patient discomfort and risk of infection.

External source radiation therapy uses high energy radiation, collimated to direct a beam into the patient to the tumor site. Although the size and strength of the radiation beam from the external source may be accurately controlled outside of the patient, the dose received by a given volume within the patient may vary because of radiation scattering and absorption by intervening tissue. For these reasons, a determination of the proper dose and placement of the dose requires an estimation of the effects of treated tissue and the tissue surrounding the treated area in scattering or attenuation of the radiation beam.

The Monte Carlo method is the most accurate method for predicting dose distributions. The path of the particles (electrons, photons, protons, or neutrons) through the patient are simulated by Monte Carlo software. Particle interactions (scattering, attenuation, and energy deposition) are simulated one at a time. The Monte Carlo method traces paths of several million particles through a patient model, the patient model accurately reflecting the three dimensional variations of electron density within the volume of the patient under study. For large numbers of source radiation particles (typically above $10^7$), the Monte Carlo method produces an accurate representation of the dose distribution. For these reasons, the Monte Carlo method is clinically preferred for the calculation of radiation dose in electron beam radiotherapy.

Unfortunately, the Monte Carlo method is extremely time consuming, taking upwards of an hour to compute a single dose distribution using current computers. One crucial and unique feature to Monte Carlo results is that the Monte Carlo method has no well-defined preset "finish" time. Instead, dose distributions can be produced at any time, even after simulating only one source particle. However, the resulting dose distributions are "noisy" (distorted), in inverse proportion to the number of source particles simulated. The Monte Carlo calculations are terminated when the noise level falls below a level deemed acceptable by the user.

Often, radiotherapy treatment planners wish to compare many dose distributions before selecting a final distribution for treatment. Hence, the need exists for a method of dose modeling which is as accurate as the Monte Carlo method but which has greater computational efficiency than the Monte Carlo method alone. This need especially exists as Monte Carlo programs are being developed for most commercial clinical systems.

More generally, the problem of noise is inherent in all Monte Carlo calculations that produce values on a grid. The problem of noise exists whether the grid elements are regularly spaced or irregularly spaced. For these reasons, there also exists a need to reduce noise and provide an accurate and computationally efficient estimate for Monte Carlo calculations in general. The present invention also satisfies this need, providing a method hereafter referred to as Monte Carlo denoising.

SUMMARY OF THE INVENTION

The present invention provides an estimate of an actual radiation dose distribution by reducing noise (denoising) from raw results of Monte Carlo generated dose distributions. The resulting denoised dose distribution more quickly and efficiently converges to the required level of accuracy for radiotherapy treatment planning than Monte Carlo calculations alone, and at a reduced computational cost. Optimal denoising reduces Monte Carlo run times by a factor of at least 3 to 6.

The present invention provides a method of accounting for details of the radiation source geometry and materials, and local changes in density of the patient at different points in the irradiated volume. This is done by denoising Monte Carlo dose distributions without significantly increasing the running time or introducing distortions to the underlying dose distributions.

The insight underlying the present invention is that a true (noiseless) radiation dose distribution is smoother (more spatially coherent) than a raw Monte Carlo result. In the present invention, it is the dose distribution itself that is accurately smoothed to reduce noise while not distorting the true underlying (signal) dose distribution.

It is our novel insight into the details of radiation transport physics which indicates that denoising is feasible and desirable (Deasy, June 2000, Denoising of electron beam Monte Carlo dose distributions using digital filtering techniques, *Physics in Medicine and Biology*, 45:1765–1779), which publication is incorporated in its entirety herein by reference. In simple terms, diffusive radiation transport implies that the actual dose distribution is smooth, whereas the Monte Carlo result without denoising contains statistical fluctuations which are more rough than the expected underlying dose distribution. Therefore, appropriate denoising techniques can be used to reduce the higher frequency noise of Monte Carlo results while not distorting the true underlying (signal) dose distribution.

In one aspect of the present invention, a method and an apparatus for accomplishing the method is provided where a raw Monte Carlo data distribution D0 (D0 everywhere refers to the raw Monte Carlo result) is first obtained and then denoised to produce a denoised distribution D1 (D1 everywhere refers to the denoised Monte Carlo result). This aspect of the present invention could be used to simply accelerate the computation of any Monte Carlo result or the present invention could be more specifically used to determine a dose distribution in a patient for radiation therapy treatment planning.

In another aspect of the present invention, denoising of the raw Monte Carlo dose distribution D0 could employ digital filtering, wavelet denoising, kernel smoothing or non-parametric regression smoothing. The digital filtering techniques could employ Binomial/Gaussian filters or local-least squares filters.

In another aspect of the present invention, denoising the raw Monte Carlo dose distribution D0 could first involve transforming the Monte Carlo dose distribution D0 by computing the square root of each data element of the Monte Carlo dose distribution D0. Digital filtering techniques could then be applied to the transformed data elements to obtain a filtered result. Then, the elements of the filtered result are squared to obtain a final best estimate of the dose distribution. The digital filtering techniques could employ Binomial/Gaussian filters or local-least squares filters. If employed, the Binomial/Gaussian filters could use a higher degree polynomial for less aggressive denoising. If employed, the local-least squares filters could use a smaller neighborhood for less aggressive denoising.

In a further aspect of the present invention, denoising the raw Monte Carlo dose distribution D0 employs either a spatially adaptive iterative filtering (SAIF) algorithm, a wavelet shrinkage threshold denoising algorithm, a spatially adaptive wavelet denoising (SAWD) algorithm, or a batch-averaged wavelet denoising (BAWD) algorithm.

In a still further aspect of the present invention, a method for determining a radiation dose pattern directed at a volume of interest in a patient includes providing to a computer a matrix T (describing an electron density for elements of the volume of interest in the patient), a subroutine (to produce a list of source particles describing a radiation source) and a Monte Carlo program (to simulate effects of the source particles). A dose accumulation matrix A is initialized to zeros. The computer then runs the Monte Carlo program to produce a dose deposition pattern for an incident source particle. The dose accumulation matrix A is then updated by adding the dose deposition pattern produced for the incident source particle. Running the Monte Carlo program and updating the dose accumulation matrix A is repeated until a predetermined stopping criteria is reached. The Monte Carlo dose distribution D0 is then set equal to the updated dose accumulation matrix A. Finally, a denoised estimate is developed for each element of the Monte Carlo data distribution D0 to produce a denoised dose distribution D1 representative of the radiation dose pattern. This aspect of the present invention could be varied by selecting an incident source particle to reduce uncertainty in a pre-determined location of a dose deposition pattern before running the Monte Carlo program. Selecting the incident source particle then becomes part of the repeated process (along with running the Monte Carlo program and updating the dose accumulation matrix A) until the pre-determined stopping criteria is reached.

In a yet further aspect of the present invention, developing the denoised estimate includes selecting an element from the Monte Carlo data distribution D0, creating a submatrix using values from the Monte Carlo data distribution D0 within a predetermined range of the selected element and multiplying the submatrix by a predetermined matrix designed to effect a least-squares fit then extracting the fit to the center element of the submatrix as the least-squares fit, and repeating these acts for each element of the Monte Carlo data distribution D0 to complete the development of the denoised estimate.

In another aspect of the present invention, developing the denoised estimate uses a variance stabilizing transformation (defined as a transformation which results in the statistical having more similar characteristics in every part of the data distribution). The variance stabilizing transformation could include computing the square root of each element of the Monte Carlo data distribution D0 to create a corresponding matrix D2. The corresponding matrix (D2) is then denoised to produce a matrix M. Every element of the matrix M is then squared to produce the denoised estimate.

In still another aspect of the present invention, developing the denoised estimate uses a statistically-based smoothing method. The statistically-based smoothing method could be the Loess method.

In yet another aspect of the present invention, developing the denoised estimate uses a curve fitting method employing Hermite polynomials for the least-squares fit. Developing the denoised estimate could also use a basis function selected from the group consisting of spline fits, spline fits with knots and weighted local least squares methods. Or, developing the denoised estimate could use a Fourier-based smoothing method. The Fourier-based smoothing method could employ a low-pass filter or a Wiener filter.

In a further aspect of the present invention, the Monte Carlo data distribution D0 is divided into parallel planes and developing the denoised estimate occurs independently for each plane.

In a still further aspect of the present invention, the Monte Carlo data distribution D0 is regridded onto a non-cartesian grid and developing the denoised estimate occurs on the non-cartesian grid with the resulting denoised dose distribution D1 being transformed back to a cartesian grid. The non-cartesian grid could be a diverging fan beam grid.

In a yet further aspect of the present invention, developing the denoised estimate uses a variable computational technique that varies to address selected portions of an image.

In another aspect of the present invention, developing the denoised estimate uses a computational technique that reduces random noise and accurately estimates underlying signal.

It is therefore one object of the invention to provide a method of dose calculation that is more computationally efficient at reaching the same level of noise than using present Monte Carlo methods alone to simulate radiation dose distributions.

It is another object of the invention to provide a method of dose calculation which reaches a lower level of dosage pattern noise than Monte Carlo methods for the same computation time.

It is a further object of the invention to accelerate any type of Monte Carlo calculation (for any purpose) to accurately represent a true underlying signal by generating and denoising a raw Monte Carlo calculation, the present invention reducing computation time relative to using present Monte Carlo methods alone.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
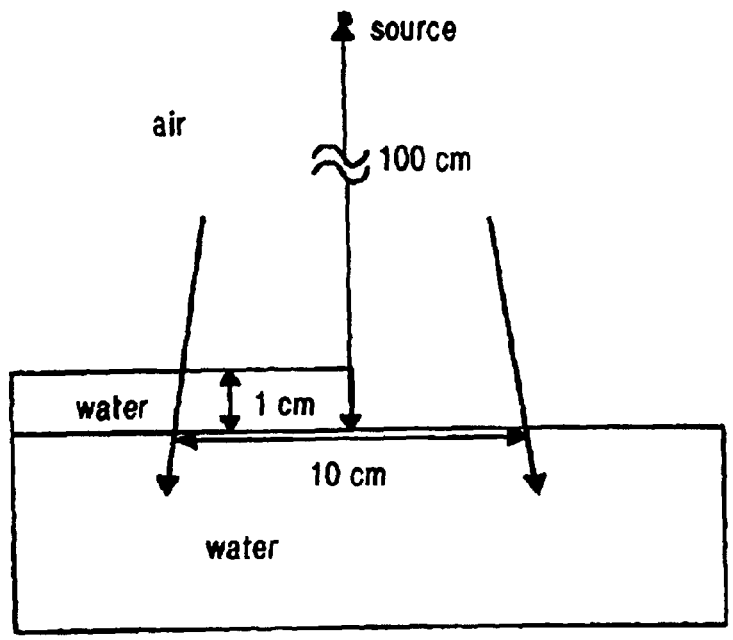
FIG. 1 illustrates a digital step-heterogeneity phantom, where electrons are transported through air before reaching the water surface, that is used as input for Monte Carlo calculations to demonstrate the denoising techniques of the present invention.

The present invention determines dosage patterns in radiotherapy where internal or external radiation sources are used to direct radiation at a volume of interest in a patient. The resulting dosage pattern within the patient is first deduced a Monte Carlo simulations tracing the path and energy deposition events of radiation particles emitted by the source. The energy deposition events are stored in memory locations associated with defined cuboid volumes of interest within the patient (voxels).

The method employs an electronic computer into which a matrix T is entered, the matrix T describing patient tissue density at the elements within the volume of interest of the patient. Radiation source particles are introduced to the matrix T, the radiation source particles having characteristics statistically consistent with the source as determined from other sources of information well known to practitioners in the art.

The dose pattern is initially estimated using Monte Carlo methods also well known to practitioners of the art. The dose to each voxel in the dose distribution is then estimated more accurately by reducing the noise in the Monte Carlo dose distribution, thereby producing a more accurate estimate of the actual smooth radiation dose pattern.

The Monte Carlo Method and Noise Characteristics

Variance at each voxel (memory location associated with a defined volume within a patient) varies approximately linearly with the corresponding absolute Monte Carlo dose. A Monte Carlo dose distribution can be considered a dose "image" measured by perfect "voxel detectors" which sum the energy deposition events. It is as though a random Gaussian variable is added to each square-root dose value, where the width of the random variable's probability density function is proportional to the dose value to which it is added. The square-root transform (i.e. taking the square-root of all dose values) is the appropriate variance stabilizing transform for such statistics (Poisson statistics). Hence the model:

$$\text{Measured Dose Array}^{1/2} = \text{True Dose Array}^{1/2} + \text{Gaussian Noise Array} \quad (1)$$

Using the model, the new array (whose values equal the square root of the dose array) consists of the signal or image to be recovered (True Dose Array$^{1/2}$), plus an additive random variable noise term of mean value zero and slowly varying—nearly constant—standard deviation.

The data model of Equation 1 of this section is known as a stationary (not a function of position) Gaussian noise model. This is the most basic data models in general technical use and it arises in many different technical areas, such as statistics, digital filtering, and digital image processing.

Denoising of Monte Carlo Electron Beam Dose Distributions via Digital Filtering

In various aspects of the present invention, four different filters (FIG. 2) are applied to four 'benchmark' style MONTE CARLO results to examine the effect of filtering on resulting dose distributions. In one embodiment the invention uses two-dimensional filtering and image adaptive methods, although it will be apparent to those skilled in the art that the present invention is equally applicable to three-dimensional filtering and image adaptive methods. The filtering techniques are applied to a variance stabilized (square-root) dose image which is transformed back to dose-space (i.e. squared) after filtering.

Denoising is aimed at computing a new image h, having elements $h_{i,j}$, such that $$h_{i,j} = \sum_{m=-k}^{k} \sum_{n=-k}^{k} a_{m,n} g_{i+n,j+m} \quad (2)$$

where the $a_{m,n}$ values are the filter coefficients, the g values are the original MC dose values, and the local convolution (smoothing) is a function of dose values within a distance ±k. The filters applied are listed in Table 0. The filter classes are of two types: Binomial/Gaussian filters (low-pass filters) and local-least squares (Savitzky-Golay) filters.

TABLE 0

Listing of digital filters. The 'order' of each Gaussian filter (GAUSS) is the number of applications of a nearest-neighbor binomial averaging that is used to derive that filter. The 'order' of each local least-squares (LLS) filter is the highest polynomial power from which that filter's coefficients are derived

| Filter name | Description |
| --- | --- |
| GAUSS_W5_O4 | Gaussian (binomial) filter of width 5 and order 4 |
| GAUSS_W3_O2 | Gaussian (binomial) filter of width 3 and order 2 |
| LLS_W11_O5 | local-least-squares filter of width 11 and order 5 |
| LLS_W5_O3 | local-least-squares filter of width 5 and order 3 |

Binomial/Gaussian filters are constructed in 1-D by repeatedly creating a new vector in which each bin is ½ the sum of nearest neighbors in the original vector of bin values. The process begins with a single nonzero bin equal to one. After each step, the new bins are centered at the borders of the old bins. The order of the filtering process is equal to the number of times this process is repeated.

In 2-D, the operation is performed separately on each row of the filter matrix, and then on each column; this cycle is repeated a number of times equal to the filter order. The filter is applied by convolution with the original image. Binomial/

Gaussian filters result in diffusion-like behavior and a Gaussian-like Fourier transfer functions. Hereafter, these filters are simply referred to as Gaussian filters.

Another interesting class of filters arises from the application of local least-squares principles. The neighborhood around each data point is fit using a polynomial fitting function, under the assumption that each data point is characterized by the same variance, according to the equation:

$$h(x, y; a_0, \ldots, b_0, \ldots, b_n) = \sum_{p=0}^{n} a_p x^p \sum_{q=0}^{m} b_q y^q, \qquad (3)$$

where unit distance is fixed as the voxel width. The order of the filter is the order of the polynomial. This equation is used to find an estimate of the center voxel in the neighborhood, which then replaces that voxel's value in the new denoised image. This process is repeated such that every voxel becomes in turn the center voxel in the application of Equation (3).

This type of filter is called a Local Least-Squares filter (LLS) and is also known as a Savitzky-Golay filter in applications to chemical spectral analysis. Previous applications of LLS filters to 2-D data are rare. We developed Mathematica code to generate LLS coefficients for an arbitrary filter width, fitted polynomial order, and data dimension (1-, 2-, or 3-D).

Figure 2:
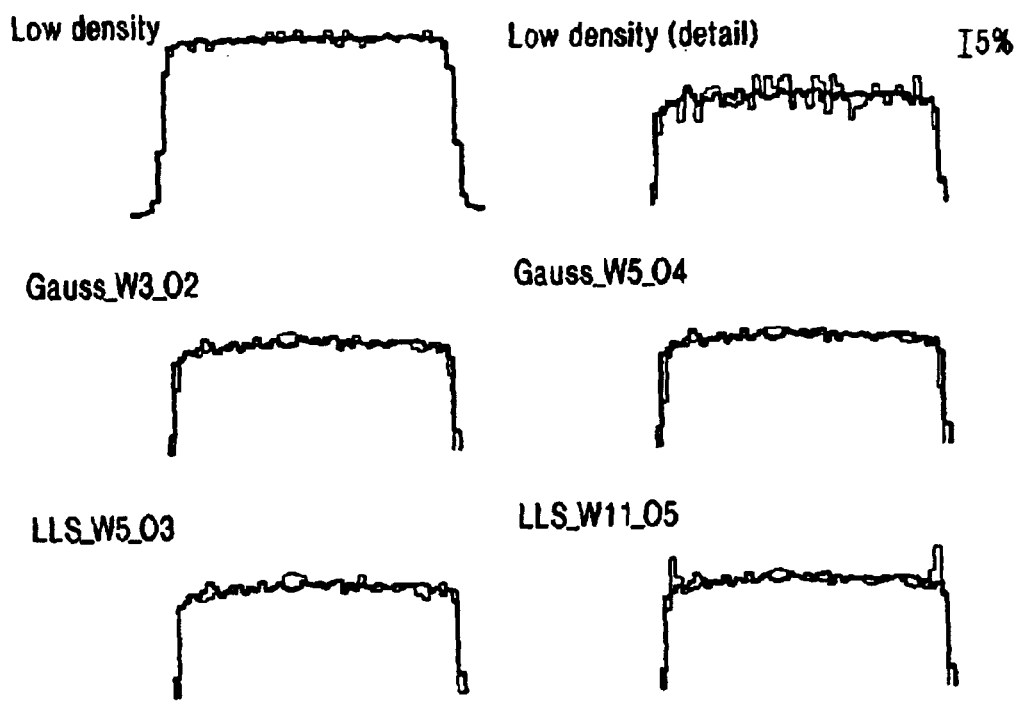
FIG. 2 illustrates profile plots demonstrating digital filtering techniques to a uniform water phantom in accordance with the present invention.
Figure 3:
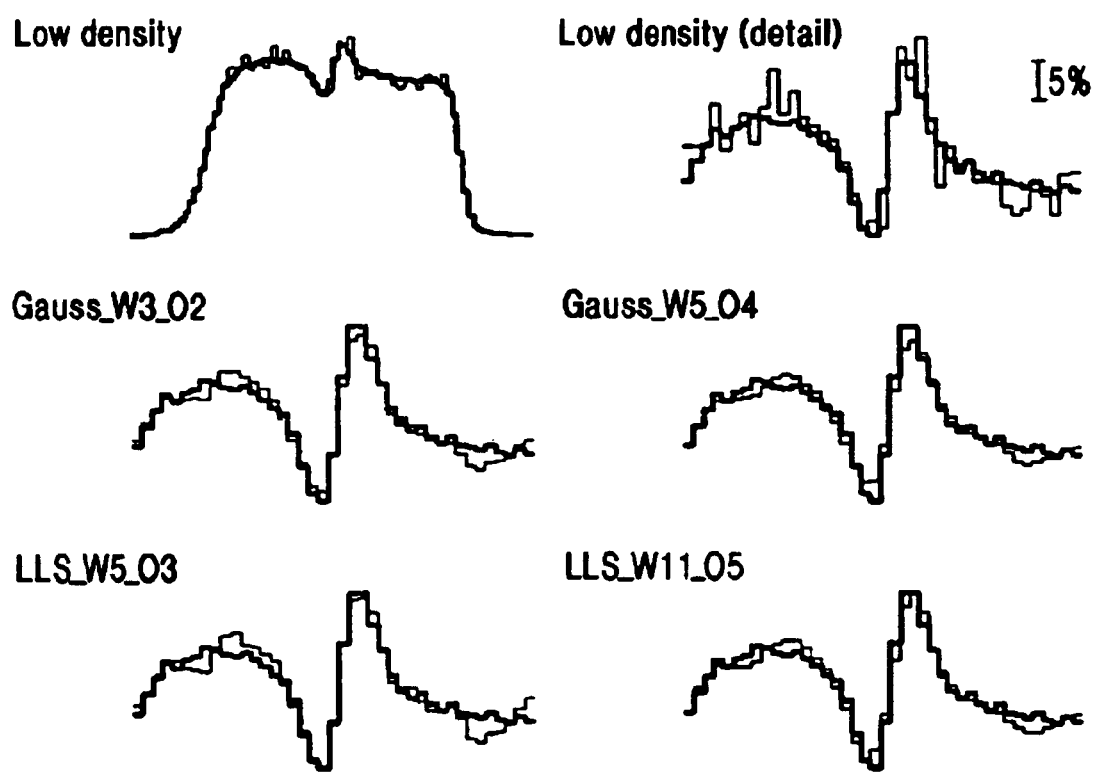
FIG. 3 illustrates profile plots demonstrating digital filtering techniques to the step-heterogeneity phantom in accordance with the present invention.

FIG. 2 shows filtered results for the uniform water phantom at a depth of 1.0 cm. Six profile plots, through the center of the dataset (column 60) are compared with the reference high density result, which is always shown as the thick line in all figures. Voxel midpoints match step midpoints in all figures. The upper pair of plots compare the high and low density results; the other four plots compare the high density result with the denoised low density result foil the indicated filter. The voxel widths are 0.2 cm. In the plateau, all the filters improve substantially on the low density result. However, there is some blurring of the sharp edges. FIG. 3 shows filtered results for the step-heterogeneity phantom of FIG. 1, are through data column 60 (one of the two centermost columns in the 2-D dose matrix), are always compared with the reference high density result (thick lines), and are at a depth of 2.55 cm below the top of the step heterogeneity. The low density dose standard deviation is 2.9%. This is an extreme test of possible heterogeneity effects. The filtering process clearly reduces noise, although some blurring of the dip-and-rise is evident for all filters except LLS_W5_O3, where it cannot be visually detected. The blurring is worst for Gauss_W5_O4.

Figure 4:
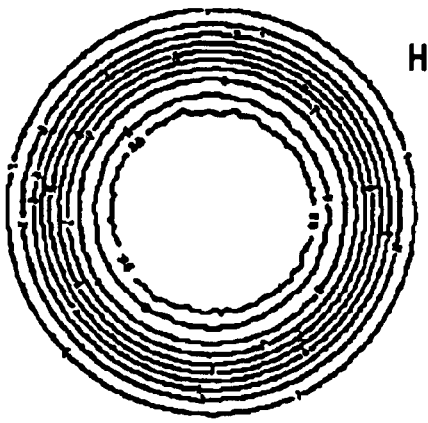
FIG. 4 illustrates contour plots of dose distributions resulting from the uniform water phantom and the heterogeneity phantom in accordance with the present invention.
Figure 4:
Figure 4:
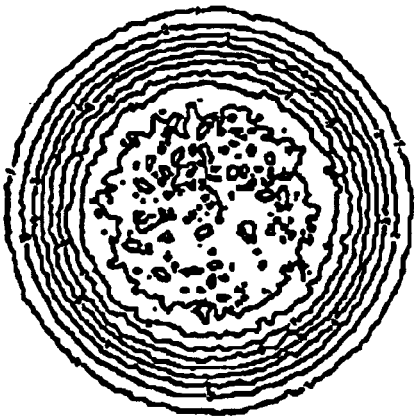
Figure 4:
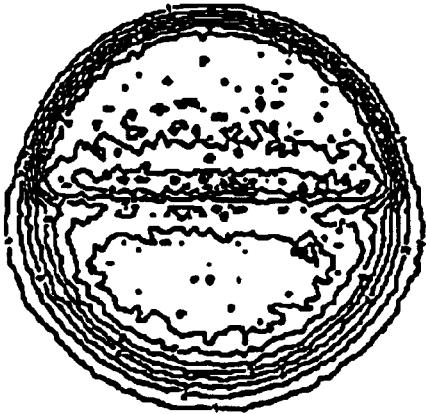
Figure 4:
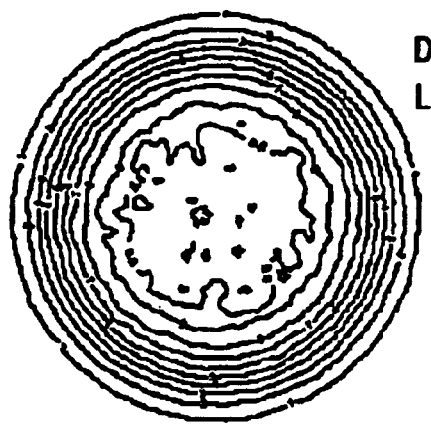
Figure 4:
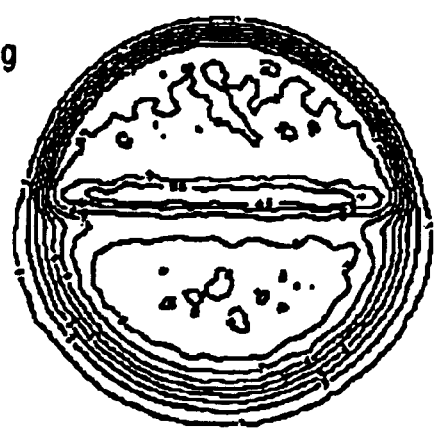

FIG. 4 shows contour plots of the dose distributions resulting from the uniform water phantom (left column) and the heterogeneity phantom (right column). The left column is from homogeneous water phantom results at a depth of 2.5 cm; the right column is from the heterogeneous phantom at a depth of 2.55 cm below the top of the step heterogeneity. These plots emphsize the difficulty in obtaining a truly 'clean' contour plot relying on 'raw' Monte Carlo results. For both phantoms, the denoised distribution (using LLS_W5_O3) is clearly cleaner visually than the low density Monte Carlo simulation. The bottom row shows the result of filtering the low density Monte Carlo data.

Denoising using digital filtering has the following advantages:

1. Improved visualization of isodose lines (FIG. 3). The ability to visually inspect the dose distribution is significantly improved using denoising filtering.

2. Suppression of spurious dose excursions (noise), as seen in the profile plots (FIGS. 2–3).

There is a trade-off between local denoising aggressiveness and systematic distortion (bias) due to blurring, as might be expected based on frequency considerations. Nonetheless, for electron beams, the filter LLS_W5_O3 is a candidate for routine filtering of clinically produced Monte Carlo dose distributions.

Spatially Adaptive Iterative Filtering (SAIF)

In another aspect of the present invention, a one-parameter denoising algorithm is employed and is directed to locally filter as aggressively as possible without distorting the underlying dose distribution. This spatially adaptive iterative filtering (SAIF) algorithm uses an array of denoised dose images by applying an array of digital filters to the raw Monte Carlo image. The best denoised image is constructed by selecting, for each voxel, the most aggressive denoising result which is statistically consistent with the original dose image. The statistical test is a chi-square comparison, over a local region, between the digital filter result and a 'lightly' denoised result which is known to be not too aggressive.

The method of spatially adaptive iterative filtering (SAIF):

Step 1. Begin with a safely denoised image (no significant bias), using the LLS_W5_O3 filter. The result is denoted $F_0$.

Step 2. Set the current best dose image (CBD) equal to $F_0$.

Step 3. Loop over increasingly aggressive filters:

Step 3.1. Denoise with the i'th filter, yielding $F_1$.

Step 3.2. Form a matrix of 'local chi-square values,' where each value is the chi-square comparison between the $F_1$ doses and the $F_0$ doses over a small region centered about that voxel.

Step 3.3. For each position in the chi-square image:

Step 3.3.1. If the local chi-square is below a preset threshold, replace that position in CBD with dose at that position in $F_1$.

Figure 5:
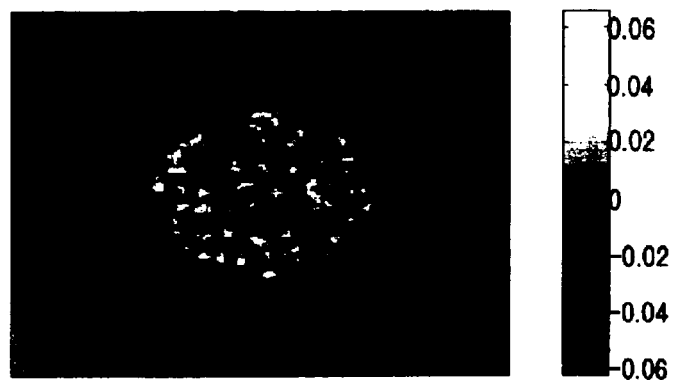
FIG. 5 illustrates application of spatially adaptive iterative filtering (SAIF) denoising algorithm to the heterogeneity phantom in accordance with the present invention.
Figure 5:
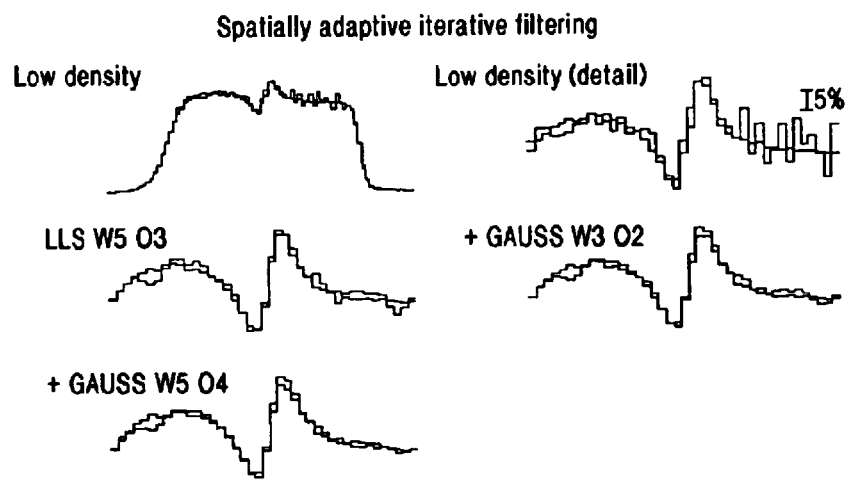
Figure 5:
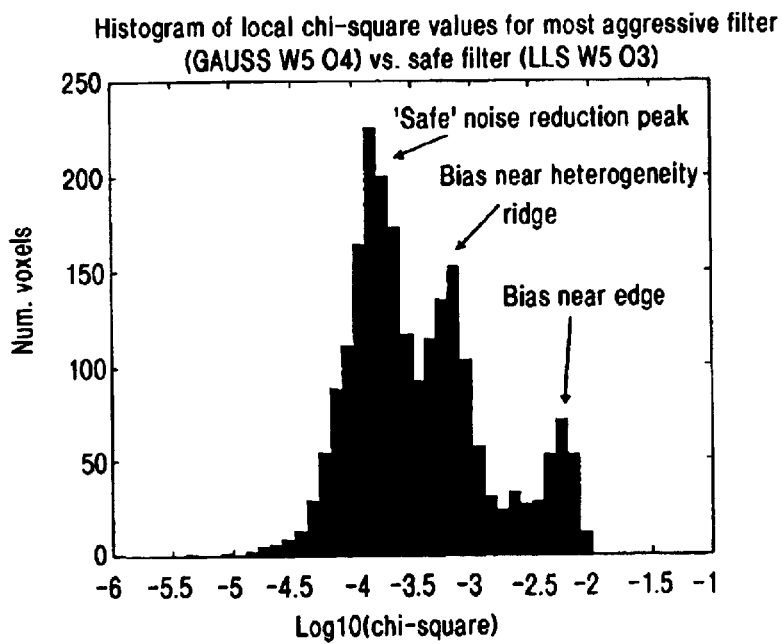

FIG. 5 illustrates an example using SAIF. The local chi-square test determines if the new aggressive filter 'fits' the image. In the FIG. 5 embodiment, an application of a (SAIF) algorithm to the electron beam heterogeneity phantom is shown. In the middle view, profile plots across the heterogeneity, at column 55, are shown. Successive results with progressively mote aggressive filters are given in the 3rd, 4th and 5th subplots. The fifth subplot is the final result. In this embodiment, dose estimates from the two more aagressive filters are only accepted if a chi-square value comparing each result and the safe (mild filter) result, over a local 3×3 region, is less than 0.0001 (the dose images are normalized to a maximum value of 1). This threshold is chosen empirically on the basis of the chi-square histogram shown in the second panel. The histogram shows how the local chi-square value is sensitive to bias which results in the two extra peaks shown. The top panel shows the difference between the resulting dose values and the "true" dose values (144 million source electrons in this case). The lack of any clear pattern in the difference indicates that the underlying smooth dose distribution is well-approximated by the SAIF algorithm.

Wavelet Denoising

In a further aspect of the present invention, wavelet shrinkage threshold denoising, or simply wavelet denoising is employed to denoise the raw Monte Carlo dose distribution. Under a wavelet transform, the data set is expressed as a linear combination or expansion in discrete wavelet coefficients. Typically, small coefficient values in the expansion represent noise, whereas larger coefficients represent spatially coherent structures. After transforming the data, the coefficients below some threshold are set to zero (in 'hard thresholding'). Then, reverse wavelet transformation is performed which converts the truncated array of wavelet coefficients back to dose array values.

In one embodiment, a Wavelet Shrinkage Denoising Algorithm with 9,7-biorthogonal filters is used, the process summarized as follows:

Step 1. Apply the square-root variance stabilizing transformation.

Step 2. Spin-cycling: Create 8 extra matrices by shifting the original by one pixel value in all the nearest neighbor directions. (This eliminates grid orientation artifacts.)

Step 3. On the original plus the 8 shifted arrays do the following:

Step 3a. Transform: perform the forward wavelet transform using the 9,7-biorthogonal filters.

Step 3b. Hard thresholding: set all wavelet coefficients smaller than a fixed fraction (denoted epsilon) of the maximum wavelet coefficient equal to zero (those coefficients are predominantly noise).

Step 3c. Inverse transform: perform the 9,7 inverse wavelet transform.

Step 4. Back-shift the 8 shifted arrays.

Step 5. Average the back-shifted arrays and the unshifted array.

Step 6. Inverse variance stabilization: square the resulting array values (step). This is the denoised dose distribution.

Figure 6:
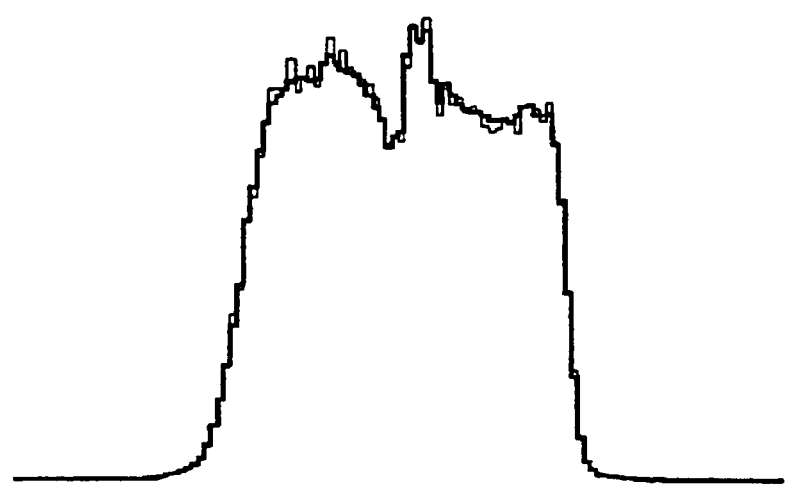
FIG. 6 illustrates denoising of the heterogeneity phantom using wavelet denoising algorithm with 9,7 biorthogonal filters in accordance with the present invention.

FIG. 6 illustrates denoising of the heterogeneity dose distribution of FIG. 1 using the wavelet denoising algorithm with 9,7-biorthogonal filters. Wavelet coefficient values less than 0.1% of the maximum wavelet coefficient value were set to zero. A computationally efficient lifting-scheme was implemented in ANSI C. The profile is through the center of the dose distribution (column 60). The thick line is the result of wavelet shrinkage denoising applied to a low-density result (thin line), which had a dose standard deviation of 2.9% before denoising. The computer time required for the denoising of this 120×120 matrix is a few milliseconds. At 0.01 threshold level, there is no perceptible bias even though noise is significantly reduced over much of the profile plot. One advantage of wavelet methods over traditional smoothing techniques is that they are locally adaptive in an automatic fashion.

Figure 7:
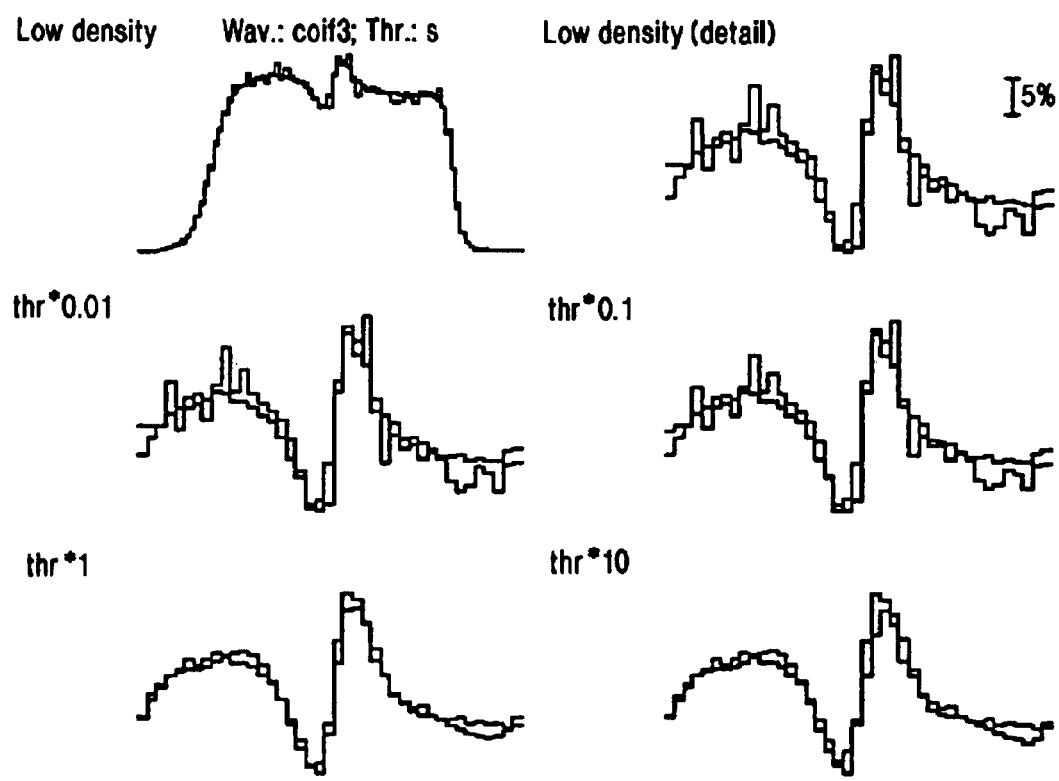
FIG. 7 illustrates denoising of the heterogeneity phantom using wavelet shrinkage denoising with third-order 'Coiflet' wavelets and soft thresholding in accordance with the present invention.

FIG. 7 illustrates an example of wavelet denoising using a 3rd order 'Coiflet' wavelet and 'soft thresholding'. Soft thresholding, like hard thresholding, sets all wavelet coefficients below a threshold to zero, but also 'shrinks' coefficients above the threshold toward zero by an amount equal in magnitude to the threshold. In the FIG. 7 embodiment, profile plots are for the step-heterogeneity phantom at a depth of 2.55 cm. Plots are through column 60 (one of the two center-most columns in the 2-D dose matrix), and are compared with the reference high density result (thick lines). The different subplots represent thresholds which have been scaled by factors of 10. The low density dose standard deviation is 2.9%. The lower left figure utilizes the optimal (or nearly optimal) threshold value.

Figure 8:
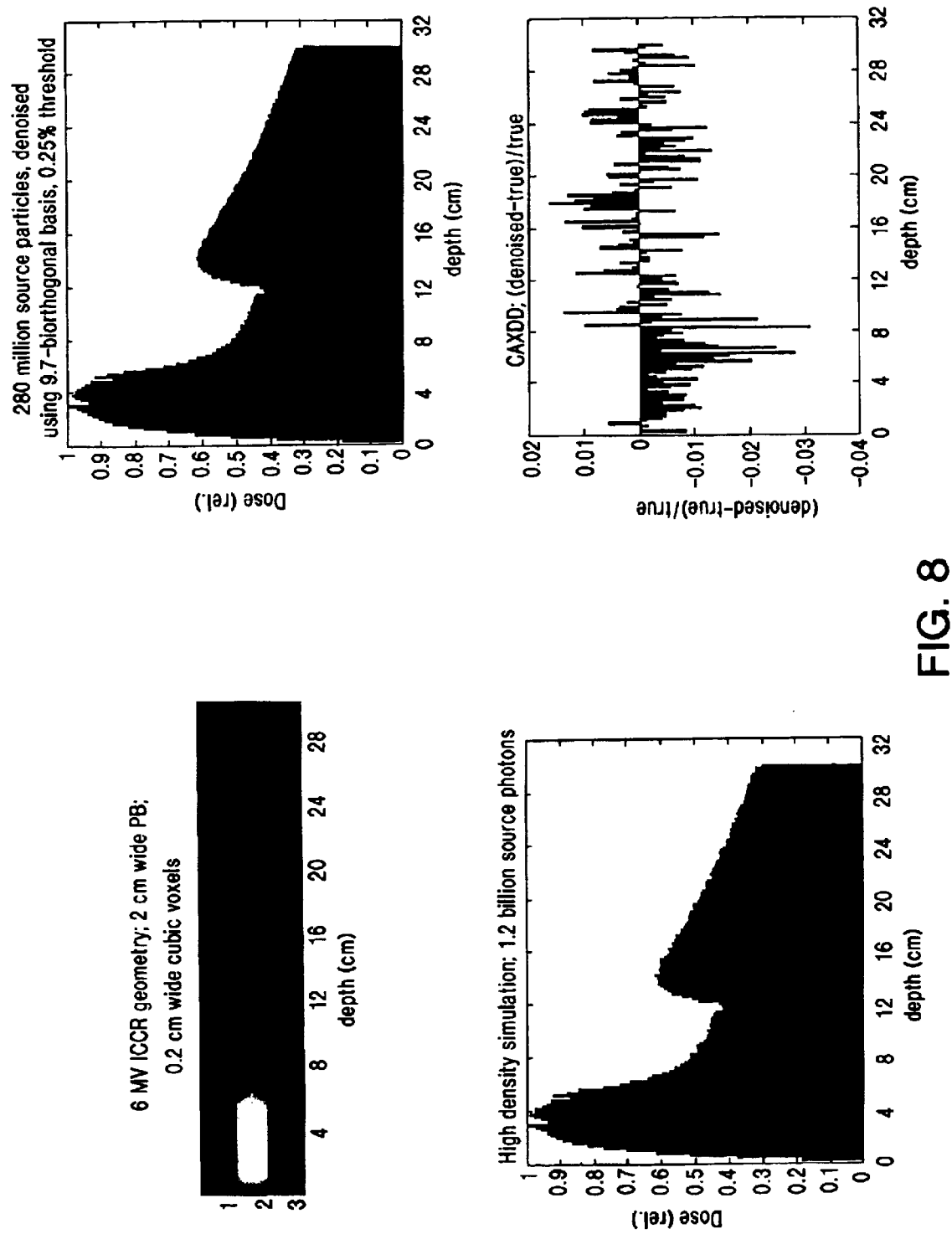
FIG. 8 illustrates wavelet denoising of three-dimensional photon dose distributions, in accordance with the present invention.

FIG. 8 illustrates wavelet denoising for 3-D photon dose distributions. The Pencil beam (PB) is denoised by denoising 2-D slices of the dose distribution in the x-z plane (i.e., a transverse-"beam direction" plane) using the 9,7-biorthogonal code. Little bias is introduced and run time is effectively reduced by at least a factor of four. In the FIG. 8 embodiment, ICCR phantom geometry was used which consists of slabs of water (0–3 cm depth), aluminum (3–5 cm), homogeneous lung-like media (5–12 cm), and water (12–32 cm). The NRCC 6 MV spectrum specified by the ICCR test is used in the ITS code. The beam is collimated to 2 cm×2 cm by an upstream lead collimator. The top shows a Grayscale central slice, the next down is a high-density central axis depth-dose with 1.2 billion source particles, the next shows a central axis depth-dose with 280 million source particles denoised with a 0.25% threshold, and the bottom illustrates a relative difference between the two. Although there may be some systematic differences, the high density result is noisier than the low density result, indicating that speed gain is greater than a factor of four.

A thorough description of wavelet denoising using 9,7-biorthogonal filters follows: The simulated dose distribution d consists of two parts, d=s+n, where s is the smooth function obtained in the limit by running the Monte Carlo simulation forever; and n is the rough function giving error due to the short Monte Carlo simulation. The data d is sampled in space, giving an array of values that are then linearly transformed into discrete wavelet coefficients, described as W(d)=W(s+n)=W(s)+W(n).

A key property of the wavelet transform is that a sampled rough function n gives values W(n) which are more nearly equal in amplitude than those of a sampled smooth function s. If n is relatively small compared to s, then any sufficiently small wavelet coefficient is more likely be part of n than s. By picking a threshold $\delta>0$ and setting $W(d)_i=0$ if $|W(d)_i|<\delta$, attenuate the n, or noise component of d. The array reconstructed from the surviving coefficients is therefore a closer approximation to s than was d=s+n.

For the key property to hold; it is necessary that the wavelet transform use a wavelet that is about as smooth as s, and thus smoother than n. The 9,7-biorthogonal wavelet is chosen, as used by the draft JPEG 2000 image compression algorithm, since images are about as smooth as true underlying dose distributions.

Approximations of Dose Distributions

Monte Carlo radiotherapy simulations produce sampled dose distributions on a finite grid. A simulated two-dimensional dose distribution on an M×N grid may be represented by a non-negative function f=f(m,n), where $0 \leq m<M$ and $0 \leq n<N$ are integer indices. Such functions may be considered approximations to distributions $\phi(x,y)$ defined on a continuum $0 \leq x,y<1$ as a superposition of basic distributions $\phi_{mn}=(x,y)$ concentrated near $$\left(\frac{m}{M}, \frac{n}{N}\right),$$

given by the formula $$\phi(x, y) = \sum_{m=0}^{M-1} \sum_{n=0}^{N-1} f(m, n)\phi_{mn}(x, y).$$

For example, characteristic functions of small regions could be taken:

$$\phi_{mn}^0(x, y) \stackrel{\text{def}}{=} \begin{cases} 1, & \text{if } \frac{m}{M} \leq x < \frac{m+1}{M} \text{ and } \frac{n}{N} \leq y < \frac{n+1}{N}; \\ 0, & \text{otherwise.} \end{cases}$$

A superposition of basic densities $\phi^0_{mn}$ is constant on $$\frac{1}{M} \times \frac{1}{N}$$

rectangles of the unit square. That is not a smooth or even continuous function.

Normal probability densities $$N[\mu, \sigma](x) \stackrel{def}{=} \frac{1}{\sqrt{2\pi}\sigma} \exp\left(-\frac{1}{2}\left[\frac{x-\mu}{\sigma}\right]^2\right),$$

of suitable mean $\mu$ and variance $\sigma$, give smooth basic functions:

$$\phi^\infty_{mn}(x, y) \stackrel{def}{=} N\left[\frac{m+\frac{1}{2}}{M}, \frac{1}{M}\right](x) \times N\left[\frac{n+\frac{1}{2}}{N}, \frac{1}{N}\right](y).$$

A superposition of densities $\phi^\infty_{mn}$ is not confined to the unit square, or any bounded region, but it has an attractive physical interpretation if the assumption is made that errors of dose measurement are normally distributed.

The represented $\phi$ will be as smooth as its basic densities, regardless of f, so a selection between $\phi^0_{mn}$ and $\phi^\infty_{mn}$ is made. Basic densities with two continuous derivatives that are "almost" confined to the unit square are selected.

Efficient Coding of Fluctuations as Wavelets

Regions of nearly constant dosage might span many grid points, with relatively small fluctuations on various scales. The amplitude and scale of each fluctuation can be used to decide what is noise and what is signal.

Independent wave function fluctuations of different sizes and positions are modeled. By approximating the original dose distribution as a superposition of particular basic densities, the fast discrete wavelet transform algorithm with 9,7-biorthogonal symmetric wavelets can be used for computing the scale and amplitude of fluctuations.

The symmetry of boundary wavelets breaks when the dimensions are not powers of 2, but both the wavelets and scaling functions remain smooth functions when reflected at the right boundary and periodized.

For efficiency, the lifting scheme is used. To reduce bias arising from the arbitrary choice of grid origin, the results of denoising the original image, and the 8 periodic shifts by one grid point: left, right, up, down, and four diagonals, are averaged. This is necessary when using the 9,7-biorthogonal symmetric wavelets, but is not necessary if other wavelet families are used as the basis of the denoising.

Discrete Wavelet Transforms

The wavelet transform is identical to that of JPEG 2000. For two-dimensional and three-dimensional arrays, the transform is applied separately along each dimension, so only the one-dimensional version is described. Let $x=x(k)$, $0 \leq k < K$ be the array of K values to be transformed. Generate a new-array $Fx=Fx(k)$, $0 \leq k < K$, by the following rule:

$$Fx(k) = \begin{cases} \sum_{n=-4}^{4} h(n) X(k-n), & \text{if } k \text{ is even;} \\ \sum_{n=-4}^{2} g(n) X(k-1-n), & \text{if } k \text{ is odd.} \end{cases} \quad (1)$$

Here $h=h(n)$ and $g=g(n)$ are the filter sequences defining the 9,7-biorthogonal wavelets. Table 1 gives their approximate values. The index ranges [−4, 4] and [−4, 2] have 9 and 7 indices, respectively. Before summing, extend the original signal x to the longer signal X by whole-sample symmetric reflection, as

TABLE 1

9,7-biorthogonal analysis filters h, g and their inverse, or synthesis filters h', g'.

| k | $h(k) = (-1)^k g'(k)$ | k | $g(k) = -(-1)^k h'(k)$ |
|---|---|---|---|
| −4, 4 | 0.03782845550699 | −4, 2 | 0.064538882628938 |
| −3, 3 | −0.02384946501938 | −3, 1 | −0.040689417609558 |
| −2, 2 | −0.11062440441842 | −2, 0 | −0.418092273222212 |
| −1, 1 | 0.37740285561265 | −1 | 0.788485616405664 |
| 0 | 0.85269867900940 | | | defined by the formula below $$X(k) = \begin{cases} x(k), & \text{if } 0 \leq k < K; \\ x(2K-2-k), & \text{if } K \leq k < 2K-1. \end{cases}$$

(Note: the above table and equation could use a higher resolution capture, but this is not absolutely necessary) X is then extended periodically by defining $X(k \pm [2K-2]) = X(k)$ for all integer indices k. The result is (2K−2)-periodic and symmetric with respect to reflection about indices 0 and K−1, with $X(k)=x(k)$ for the original indices $k=0, 1, \ldots,$ K−1. The output sequence Fx(k) is also (2K−2)-periodic and defined at all integers k, but because the filters are symmetric, a complete set of output values may be found at just the indices $0, 1, \ldots, K-1$. This allows computation of Fx in about 8K operations.

The lifting scheme reorganizes the computation of Fx to save operations. With x extended to X as before, F is performed sequentially in place as follows:

1. $X(k) \leftarrow X(k) + \alpha[X(k-1)+X(k+1)]$, for all odd k in the range $0<k<K$;
2. $X(k) \leftarrow X(k) + \beta[X(k-1)+X(k+1)]$ for all even k in the range $0 \leq k<K$;
3. $X(k) \leftarrow X(k) + \gamma[X(k-1)+X(k+1)]$, for all odd k in the range $0<k<K$;
4. $X(k) \leftarrow X(k) + \delta[X(k-1)+X(k+1)]$ for all even k in the range $0 \leq k<K$;
5. $Fx(k) \leftarrow X(k)/\zeta$, for all even k in the range $0 \leq k<K$;
6. $Fx(k) \leftarrow \zeta X(k)$, for all even k in the range $0 \leq k<K$;

TABLE 2

Lifting coefficients for 9,7-biorthogonal analysis filters.

| Coefficient | Value |
|---|---|
| $\alpha$ | −1.58613434205992 |
| $\beta$ | −0.05298011857296 |
| $\gamma$ | 0.88291107553093 |
| $\delta$ | 0.44350685204397 |
| $\zeta$ | 1.14960439886024 |

The coefficients $\{\alpha, \beta, \gamma, \delta, \zeta\}$ are given in Table 2. The resulting sequence Fx is the same as the one defined by Equation 1 of this section, but it takes only 5K operations to compute, less intermediate storage, and fewer data exchanges.

To invert F, use $\{-\alpha, -\beta, -\gamma, -\delta; 1/\zeta\}$ and apply the operations in reverse order:

1. $Y(k) \leftarrow Y(k)/\zeta$, for all even k in the range $0 \leq k<K$;
2. $Y(k) \leftarrow Y(k)/\zeta$, for all odd k in the range $0<k<K$;

3. $Y(k) \leftarrow Y(k) - \delta[Y(k-1)+Y(k+1)]$, for all even k in the range $0 \leq k < K$;
4. $Y(k) \leftarrow Y(k) - \gamma[Y(k-1)+Y(k+1)]$, for all odd k in the range $0 < k < K$;
5. $F^1 y(k) \leftarrow Y(k) - \beta[Y(k-1)+Y(k+1)]$, for all even k in the range $0 \leq k < K$;
6. $F^1 y(k) \leftarrow Y(k) - \alpha[Y(k-1)+Y(k+1)]$, for all odd k in the range $0 < k < K$.

The analog of Equation 1 of this section for $F^1 y$ is $$F^{-1}y(n) = \sum_{k \in K_0(n)} h'(2k-n)Y(2k) + \sum_{k \in K_1(n)} g'(2k-n)Y(2k+1), \quad (2)$$

where Y is the same extension of y as X is of x. The inverse filters h', g' are given in Table 1. The index ranges are $K_0(n)=\{k:-4 \leq 2k-n \leq 2\}$ and $K_1(n)=\{k:-4 \leq 2k-n \leq 4\}$, for $n=0,1,\ldots,K-1$.

Each even-indexed element Fx(2k) is a weighted average of x over nine grid points near 2k, with the weights being the filter coefficients. It is also the amplitude of the basic distribution shaped, but twice as wide, that best represents the signal near 2k. That original signal differs from this wide base by fluctuations on the scale of two grid points. The amplitudes of those fluctuation wavelets are given by the odd-indexed elements Fx(1), Fx(3), ..., etc.

To compute a one-dimensional wavelet transform on a signal x, apply F, retain the odd-indexed values, extract the even-indexed values to another array of about half the length, call that new array x, and repeat until x contains just a single number:

1. Let j=1.
2. Compute y(k)=Fx(k), k=0,1, ..., K-1;
3. Extract $D_j(k)=y(2k+1)$ for all indices k with $0<2k+1<K$.
4. Replace x(k)=y(2k) for all indices k with $0 \leq 2k<K$.
5. Replace $K \leftarrow K/2$ if K is even, or $K \leftarrow (K+1)/2$ if K is odd. This is the number of elements written to x at step 4.
6. If K>1, then increment $j \leftarrow j+1$ and go to step 2. Otherwise, stop.

At the termination of the above algorithm, the discrete wavelet transform of the original signal is stored in the arrays $D_1, D_2, \ldots, D_j$, plus y(0). The values in $D_j$ are the amplitudes of fluctuations of the signal at scales of $2^J$ grid points; y(0) contains the average value of the signal. J is the depth of the wavelet transform, the maximum value of j in the algorithm above, and is the least integer such that $2^j \geq K$.

A standard way to index wavelet coefficients so as to preserve both size and position information for the fluctuations is to let $W(x)=(y(0); D_j, D_2, \ldots, D_1)$, the concatenation of the fluctuation arrays in the reverse order of their computation.

Approximation and De-Noising

The root mean square sum is used to measure the size of functions on grids M.

$$\|f\| \stackrel{def}{=} \sqrt{\frac{1}{|M|} \sum_{m \in M} |f(m)|^2}.$$

Here $|M|$ is the number of points in the grid. With this definition, the quantity $\|\hat{f}-f\|$ is the RMS, or root mean square error between estimator $\hat{f}$ and exact value f, while $\|\hat{f}-f\|/\|f\|$ is the relative RMS error. To say n is relatively small compared to s will mean $\|n\| << \|s\|$.

Define the thresholding function $T=T_\epsilon[x]$ for a function x on M by letting $a=\max\{|x(m)|:m \in M\}$ and then setting $$T_\epsilon[x](m) = \begin{cases} 0, & \text{if } |x(m)| < \epsilon a, \\ x(m), & \text{otherwise.} \end{cases}$$

Thresholding with small $\epsilon$ is a nonlinear transformation, but is close to the identity in the sense that $$\frac{|x(m) - T_\epsilon[x](m)|}{\|x\|} \leq \epsilon,$$

for every $m \in M$.

It remains to choose the threshold. Let $\in$ be a fixed positive parameter, let $0 \in M$ be the origin in the grid M, and let $0 \in M$ be some fixed grid point. Designate the wavelet transform of $f$ by $W(f)=\{W(f)_m:m \in M\}$, with $W(f)_0$ being the single average coefficient, previously called y(0). The following algorithm is performed:

1. Translate the function $f$ to $f_o$, so that $f_o(0)=f(o)$.
2. Compute the wavelet transform $y_o \leftarrow W(f_o)$.
3. Apply $\epsilon$—thresholding $z_o(m) \leftarrow T(y_o(m))$ for all $m \neq 0$.
4. Compute the inverse wavelet transform $x_o \leftarrow W^{-1}(z_o)$.
5. Translate the function $x_o$ to x, so that $x(o)=x_o(0)$.

Let O be the origin of M and its nearest neighbors, then average together all the x's obtained for different choices of $o \in O$. In the one-dimensional case, $O=\{-1, 0, +1\}$, while in the two-dimensional case O is the nine-point set $\{-1, 0,+1\} \times \{-1, 0,+1\}$. Denote by $E(f, \epsilon)$ the average of the x's produced by all the shifts of the original f.

Suppose that d=s+n is an approximation to the dose distribution s. Assume that s is known because the Monte Carlo simulation has been run long enough to approximate s adequately. Obtain several independent d's by selecting short disjoint segments of this long simulation. These are all nonnegative functions on the same grid M, so perform the variance-stabilizing square-root operation and get all estimator for s from $$\left(E(\sqrt{d}, \epsilon)\right)^2.$$

The threshold $\in$ that minimizes the RMS error $$\left\|\left(E(\sqrt{d}, \epsilon)\right)^2 - s\right\|$$

for each of the short segments d that comprise the long run, is found by a bisection search. The average of these thresholds is an estimator for the best threshold to use in all similar-size simulations.

Threshold Dependence on Run Length

Suppose that a Monte Carlo simulation of length R produces an adequate approximation to the limit dose distribution s. Let $\epsilon$ (r) be the optimal threshold for runs of length r<<R, namely the average of the minimizers of $\Delta(r)$ for each short run. Similarly, let be the average of the errors $$\left\|\left(E(\sqrt{d}, \epsilon)\right)^2 - s\right\|$$

taken over the R/r runs d of length r that comprise the run that produced s.

Spatially Adaptive Wavelet Denoising Algorithm (SAWD):

In another aspect of the present invention, a spatially adaptive wavelet denoising algorithm is employed, which adapts the local wavelet threshold according to a local measure of goodness of fit. In essence, the most aggressive denoising (which shows no significant bias compared to the safely/unaggressively denoised image) is locally applied.

The Method of spatially adaptive wavelet denoising (SAWD):

Step 1. Begin with a safely denoised image (no significant bias), implemented by wden9_7.c computer code or the like with a threshold of 0.05% for this step. The result is denoted $F_0$.

Step 2. Set the current best dose image (CBD) equal to $F_0$.

Step. 3 Loop over increasing thresholds (for example: [0.1, 0.15, 0.2, 0.25]):

Step 3.1. Denoise with the wavelet denoising wden9_7 software and the i'th threshold, yielding $F_1$.

Step 3.2. Form a matrix of 'local chi-square values,' where each value is the chi-square comparison between the $F_1$ doses and the $F_0$ doses over a small region centered about that voxel.

Step 3.3. For each position in the chi-square image:

Step 3.3.1. If the local chi-square is below a preset threshold, replace that position in CBD with the value in $F_i$.

Batch-averaged Wavelet Denoising:

In another aspect of the present invention, a Batch-averaged wavelet algorithm is employed to denoise the raw Monte Carlo dose distribution.

The Method of Batch-averaged wavelet denoising (BAWD):

Step 0. Divide the MC computation into N (say, 10) equal batches. For each batch apply the following wavelet denoising algorithm (implemented in wden9_7.c computer code or the like):

Step 1. Apply the square-root variance stabilizing transformation.

Step 2. Spin-cycling: Create 8 extra matrices by shifting the original by one pixel value in all the nearest neighbor directions. (This eliminates grid orientation artifacts.)

Step 3. On the original plus the 8 shifted arrays do the following:

Step 3a. Transform: perform the forward wavelet transform using the 9,7-biorthogonal filters.

Step 3b. Hard thresholding: set all wavelet coefficients smaller than a fixed fraction of the maximum wavelet coefficient (denoted epsilon) equal to zero (those coefficients are predominantly noise).

Step 3c. Inverse transform: perform the 9,7 inverse wavelet transform.

Step 4. Back-shift the 8 shifted arrays.

Step 5. Average the back-shifted arrays and the unshifted array.

Step 6. Inverse variance stabilization: square the resulting array values (step). This is the denoised dose distribution.

Step 7. End loop over batches (go to Step 0 if more batches are required).

Step 8. Return the average of the denoised batch solutions as the final answer.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A method for accelerating computation of Monte Carlo results, comprising the steps of:
   a. obtaining a Monte Carlo data distribution; and
   b. locally denoising the Monte Carlo data distribution based upon local characteristics of the distribution, thereby producing a denoised distribution.

2. The method of claim 1, wherein the denoised distribution has a reduced computational cost relative to Monte Carlo calculations without denoising.

3. The method of claim 1, wherein locally denoising the Monte Carlo data distribution employs:
   a spatially adaptive iterative filtering (SAIF) algorithm;
   a wavelet shrinkage threshold denoising algorithm;
   a spatially adaptive wavelet denoising (SAWD) algorithm; or
   a batch-averaged wavelet denoising (BAWD) algorithm.

4. The method of claim 1, wherein locally denoising the Monte Carlo data distribution provides more aggressive local denoising where the data distribution is not rapidly fluctuating and less aggressive local denoising where the data distribution is rapidly fluctuating.

5. A method for determining a dose distribution in a patient for radiation therapy treatment planning, the method comprising the steps of:
   obtaining a raw Monte Carlo dose distribution; and
   denoising the raw Monte Carlo dose distribution, thereby producing a denoised dose distribution representative of the dose distribution in the patient, wherein denoising the raw Monte Carlo dose distribution includes the steps of:
      transforming the Monte Carlo dose distribution by computing the square root of each data element of the Monte Carlo dose distribution;
      applying digital filtering techniques to the transformed data elements to obtain a filtered result; and
      squaring elements of the filtered result to obtain a final best estimate of the dose distribution.

6. The method of claim 5, wherein the digital filtering techniques employ Binomial/Gaussian filters.

7. The method of claim 6, wherein less aggressive denoising is accomplished by using a higher degree polynomial.

8. The method of claim 5, wherein the digital filtering techniques employ local-least squares filters.

9. The method of claim 8, wherein less aggressive denoising is accomplished by using a smaller neighborhood in least squares fitting.

10. A method for determining a dose distribution in a patient for radiation therapy treatment planning, the method comprising the steps of:
    obtaining a raw Monte Carlo dose distribution; and
    denoising the raw Monte Carlo dose distribution using a spatially adaptive iterative filtering (SAIF) algorithm, thereby producing a denoised dose distribution representative of the dose distribution in the patient.

11. A method for determining a dose distribution in a patient for radiation therapy treatment planning, the method comprising the steps of:
    obtaining a raw Monte Carlo dose distribution; and
    denoising the raw Monte Carlo dose distribution using a wavelet shrinkage threshold denoising algorithm, thereby producing a denoised dose distribution representative of the dose distribution in the patient.

12. A method for determining a dose distribution in a patient for radiation therapy treatment planning, the method comprising the steps of:
   obtaining a raw Monte Carlo dose distribution; and
   denoising the raw Monte Carlo dose distribution using a spatially adaptive wavelet denoising (SAWD) algorithm, thereby producing a denoised dose distribution representative of the dose distribution in the patient.

13. A method for determining a dose distribution in a patient for radiation therapy treatment planning, the method comprising the steps of:
   obtaining a raw Monte Carlo dose distribution; and
   denoising the raw Monte Carlo dose distribution using a batch-averaged wavelet denoising(BAWD) algorithm, thereby producing a denoised dose distribution representative of the dose distribution in the patient.

14. A method for determining a radiation dose pattern directed at a volume of interest in a patient, the method comprising the steps of:
   a. prriding a matrix T describing an electron density for elements of the volume of interest in the patient;
   b. providing a subroutine to produce a list of source particles describing a radiation source;
   c. providing a Monte Carlo program to simulate effects of the source particles;
   d. initializing a dose accumulation matrix A to zeros;
   e. running the Monte Carlo program to produce a dose deposition pattern for an incident source particle;
   f. updating the dose accumulation matrix A by adding the dose deposition pattern produced for the incident source particle;
   g. repeating steps (e) and (I) until reaching a predetermined stopping criteria;
   h. setting the Monte Carlo data distribution D0 equal to the updated dose accumulation matrix A; and
   i. developing a denoised estimate for each element of the Monte Carlo data distribution D0 to produce a denoised dose distribution D1 representative of the radiation dose pattern, wherein developing the denoised estimate involves:
      a variance stabilizing transformation;
      a Loess smoothing method;
      a curve fitting method employing Hermite polynomials for the least-squares
      a basis function selected from the group consisting of spline fits, spline fits with knots and weighted local least squares methods;
      a Fourier-based smoothing method; or
      a variable computational technique that varies to address selected portions of an image.

15. The method of claim 14, wherein the Fourier-based smoothing method employs application of a low-pass filter.

16. The method of claim 14, wherein the Fourier-based smoothing method employs application of a Wiener filter.

17. The method of claim 14, wherein the variance stabilizing transformation is a function designed to alter statistical properties of the dose deposition pattern produced by running the Monte Carlo program.

18. The method of claim 14, wherein the variance stabilizing transformation includes the steps of:
   a. computing the square root of each element of the Monte Carlo data distribution D0 of step (h) to create a corresponding matrix D2;
   b. denoising the corresponding matrix (D2) to produce a matrix M; and
   c. computing the square of every element of the matrix M to produce the denoised estimate.

19. A method for determining a dose distribution in a patient for radiation therapy treatment planning, comprising the steps of:
   a. obtaining a raw Monte Carlo dose distribution; and
   b. denoising the raw Monte Carlo dose distribution, thereby producing a denoised dose distribution representative of the dose distribution in the patient, wherein denoising employs:
      a variance stabilizing transformation;
      a Loess smoothing method;
      a curve fitting method employing Hermite polynomials for the least-squares fit;
      a basis function selected from the group consisting of spline fits, spline fits with knots and weighted local least squares methods;
      a Fourier-based smoothing method; or
      a variable computational technique that varies to address selected portions of an image.

20. A method for determining a dose distribution in a patient for radiation therapy treatment planning, comprising the steps of:
   a. obtaining a Monte Carlo dose distribution; and
   b. denoising the Monte Carlo dose distribution using wavelet denoising, kernel smoothing or non-parametric regression smoothing.

21. A method for determining a radiation dose pattern directed at a volume of interest in a patient, the method comprising the steps of:
   a. providing a matrix T describing an electron density for elements of the volume of interest in the patient;
   b. providing a subroutine to produce a list of source particles describing a radiation source;
   c. providing a Monte Carlo program to simulate effects of the source particles;
   d. initializing a dose accumulation matrix A to zeros;
   e. running the Monte Carlo program to produce a dose deposition pattern for an incident source particle;
   f. updating the dose accumulation matrix A by adding the dose deposition pattern produced for the incident source particle;
   g. repeating steps (e) and (f) until reaching a predetermined stopping criteria;
   h. setting the Monte Carlo data distribution D0 equal to the updated dose accumulation matrix A; and
   i. developing a denoised estimate for each element of the Monte Carlo data distribution D0 to produce a denoised dose distribution D1 representative of the radiation dose pattern, wherein developing the denoised estimate includes the steps of:
      1. selecting an element from the Monte Carlo data distribution D0 of step (h);
      2. creating a submatrix using values from the Monte Carlo data distribution D0 within a predetermined range of the selected element;
      3. multiplying the submatrix by a predetermined matrix designed to effect a least-squares fit then extracting the fit to the center element of the submatrix as the least-squares fit; and
      4. repeating steps (1) through (3) for each element of the Monte Carlo data distribution D0 to complete the development of the denoised estimate.

22. A method for determining a radiation dose pattern directed at a volume of interest in a patient, the method comprising the steps of:

providing a matrix T describing an electron density for elements of the volume of interest in the patient;

providing a subroutine to produce a list of source particles describing a radiation source;

c. providing a Monte Carlo program to simulate effects of the source particles;

d. initializing a dose accumulation matrix A to zeros;

e. running the Monte Carlo program to produce a dose deposition pattern for an incident source particle;

f. updating the dose accumulation matrix A by adding the dose deposition pattern produced for the incident source particle;

steps (e) and (f) until reaching a predetermined stopping criteria;

h. setting the Monte Carlo data distribution D0 equal to the updated dose accumulation matrix A; and j. developing a denoised estimate for each element of the Monte Carlo data distribution D0 to produce a denoised dose distribution D1 representative of the radiation dose pattern, wherein the Monte Carlo data distribution D0 of step (h) is:
1. divided into parallel planes and developing the denoised estimate occurs independently for each plane, or;
2. regridded onto a non-cartesian grid, where developing the denoised estimate occurs on the non-cartesian grid and resulting denoised dose distribution D1 is transformed back to a cartesian grid.

23. The method of claim 22, wherein the non-cartesian grid is a diverging fan beam grid.

24. A computer readable medium that configures a computer to perform a method that accelerates computation of Monte Carlo results, the method comprising the steps of:
   a. obtaining a Monte Carlo data distribution D0; and
   b. locally denoising the Monte Carlo data distribution based upon local characteristics of the distribution, thereby producing a denoised distribution.

25. The computer readable medium of claim 24, wherein locally denoising the Monte Carlo data distribution employs:
   a spatially adaptive iterative filtering (SAW) algorithm;
   a wavelet shrinkage threshold denoising algorithm;
   a spatially adaptive wavelet denoising (SAWD) algorithm; or
   a batch-averaged wavelet denoising (BAWD) algorithm.

26. The computer readable medium of claim 24, wherein locally denoising the Monte Carlo data distribution provides more aggressive local denoising where the data distribution is not rapidly fluctuating and less aggressive local denoising where the data distribution is rapidly fluctuating.

27. A computer readable medium that configures a computer to perform a method that determines a dose distribution in a patient for radiation therapy treatment planning, the method comprising the steps of:
   a. obtaining a raw Monte Carlo dose distribution; and
   b. denoising the raw Monte Carlo dose distribution, thereby producing a denoised dose distribution representative of the dose distribution in the patient, wherein denoising employees:
      a variance stabilizing transformation;
      a Loess smoothing method;
      a curve fitting method employing Hermite polynomials for the least-squares fit;
      a basis function selected from the group consisting of spline fits, spline fits with knots and weighted local least squares methods;
      a Fourier-based smoothing method; or
      variable computational technique that varies to address selected portions of an image.

28. A computer readable medium that configures a computer to perform a method that determines a dose distribution in a patient for radiation therapy treatment planning, the method comprising the steps of:
   a. obtaining a Monte Carlo dose distribution; and
   b. denoising the Monte Carlo dose distribution using wavelet denoising, kernel smoothing or non-parametric regression smoothing.

29. A computer readable medium that configures a computer to perform a method that determines a radiation dose pattern directed at a volume of interest in a patient, the method comprising the steps of:
   a. providing a matrix T describing an electron density for elements of the volume of interest in the patient;
   b. providing a subroutine to produce a list of source particles describing a radiation source;
   c. providing a Monte Carlo program to simulate effects of the source particles;
   d. initializing a dose accumulation matrix A to zeros;
   e. running the Monte Carlo program to produce a dose deposition pattern for an incident source particle;
   f. updating the dose accumulation matrix A by adding the dose deposition pattern produced for the incident source particle;
   g. repeating steps (e) and (f) until reaching a predetermined stopping criteria;
   h. setting the Monte Carlo data distribution D0 equal to the updated dose accumulation matrix A; and
   i. developing a denoised estimate for each element of the Monte Carlo data distribution D0 to produce a denoised dose distribution D1 representative of the radiation dose pattern, wherein developing the denoised estimate involves:
      a variance stabilizing transformation;
      a Loess smoothing method;
      curve fitting method employing Hermite polynomials for the least-squares fit;
      a basis function selected from the group consisting of spline fits, spline fits with knots and weighted local least squares methods;
      a Fourier-based smoothing method; or
      variable computational technique that varies to address selected portions of an image.

30. A computer readable medium that stores a program to accelerate computation of Monte Carlo results, the program comprising:
   a. means for obtaining a Monte Carlo data distribution; and
   b. means for locally denoising the Monte Carlo data distribution based upon local characteristics of the distribution, thereby producing a denoised distribution.

31. A computer readable medium that stores a program to determine a dose distribution in a patient for radiation therapy treatment planning, the program comprising:
   a. means for obtaining a Monte Carlo dose distribution- and
   b. means for locally denoising the Monte Carlo dose distribution based upon local characteristics of the distribution, thereby producing a denoised dose distribution representative of the dose distribution in the patient.

32. A method for accelerating computation of Monte Carlo results, the method comprising the steps of:
   obtaining a Monte Carlo data distribution; and
   denoising the Monte Carlo data distribution using:
      a variance stabilizing transformation;
      a Loess smoothing method;
      a curve fitting method employing Hermite polynomials for the least-squares fit;
      a basis function selected from the group consisting of spline fits, spline fits with knots and weighted local least squares methods;
      a Fourier-based smoothing method; or
      a variable computational technique that varies to address selected portions of an image.

33. A computer readable medium that configures a computer to perform a method that accelerates computation of Monte Carlo results, the method comprising the steps of:
   obtaining a Monte Carlo data distribution; and
   denoising the Monte Carlo data distribution using:
      a variance stabilizing transformation;
      a Loess smoothing method;
      a curve fitting method employing Hermite polynomials for the least-squares fit;
      a basis function selected from the group consisting of spline fits, spline fits with knots and weighted local least squares methods;
      a Fourier-based smoothing method; or
      a variable computational technique that varies to address selected portions of an image.

* * * * *

UNITED STATES PATENT AND TRADEMARK OFFICE
CERTIFICATE OF CORRECTION

PATENT NO. : 6,792,073 B2
DATED : September 14, 2004
INVENTOR(S) : Joseph O. Deasy and Mladen Victor Wickerhauser It is certified that error appears in the above-identified patent and that said Letters Patent is hereby corrected as shown below:

Column 17,
Line 21, delete "ppriding" and replace with -- providing --.
Line 34, delete "(I)" and replace with -- (f) --.

Column 20,
Line 44, before "curve fitting method" insert -- a --.

Signed and Sealed this

Twenty-second Day of February, 2005

JON W. DUDAS
*Director of the United States Patent and Trademark Office*